Figure 1:
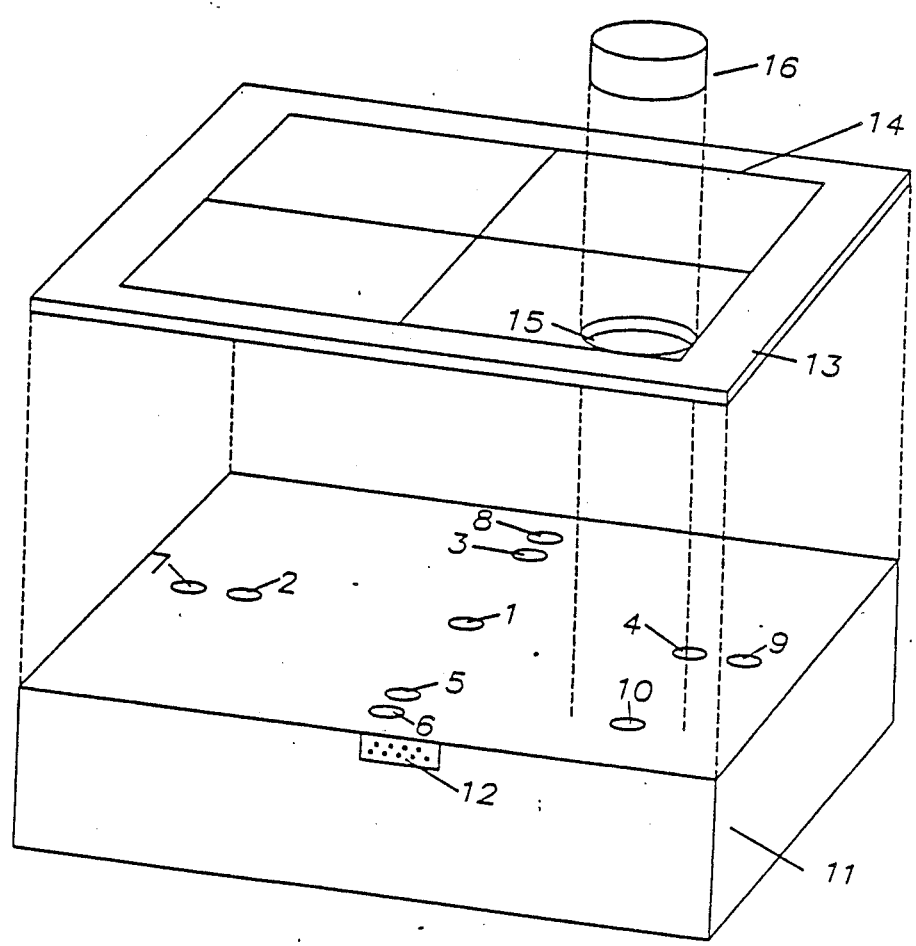

United States Patent [19]

Westerlund

[11] Patent Number: 4,988,866
[45] Date of Patent: Jan. 29, 1991

[54] MEASURING DEVICE FOR CHECKING RADIATION FIELDS FROM TREATMENT MACHINES FOR RADIOTHERAPY

[76] Inventor: Kjell B. Westerlund, Mälarvägen 8, S-756 53 Upsala, Sweden

[21] Appl. No.: 458,628
[22] PCT Filed: Jul. 19, 1988
[86] PCT No.: PCT/SE88/00385
 § 371 Date: Jan. 19, 1990
 § 102(e) Date: Jan. 19, 1990
[87] PCT Pub. No.: WO89/00703
 PCT Pub. Date: Jan. 26, 1989

[30] Foreign Application Priority Data
 Jul. 21, 1987 [SE] Sweden .................. 8702926

[51] Int. Cl.⁵ .................. G01T 1/161; A61N 5/10
[52] U.S. Cl. .................. 250/252.1; 250/389; 250/374; 250/370.06
[58] Field of Search .................. 250/370.01, 370.06, 250/370.07, 374, 389, 252.1 R; 328/206, 207, 97

[56] References Cited

U.S. PATENT DOCUMENTS

| | | | |
|---|---|---|---|
| 2,933,610 | 4/1960 | Ress | 250/385.1 |
| 3,942,012 | 3/1976 | Boux | 250/385 |
| 4,206,355 | 6/1980 | Boux | 250/385 |
| 4,290,012 | 9/1981 | Berte et al. | 324/71.3 |
| 4,300,050 | 11/1981 | Hizo et al. | 250/374 |
| 4,568,828 | 2/1986 | Collica | 250/352.1 |

FOREIGN PATENT DOCUMENTS

0754998 10/1984 U.S.S.R. .................. 378/97

Primary Examiner—Janice A. Howell
Assistant Examiner—Drew A. Dunn
Attorney, Agent, or Firm—Bacon & Thomas

[57] ABSTRACT

A measuring device for checking of radiation fields from treatment machines for radiotherapy, comprising a measuring block (11) containing radiation detectors (1-10) arranged under a cover plate (13) provided with field marking lines (14) and energy filter (16), said detectors being connected to a readout unit for signal processing and presentation of measurement values, the arrangement of the radiation detectors in the block and the signal processing in the readout unit being such that the dose monitor calibration, the homogeneity of the radiation field, the geometrical correspondence of the radiation field and the light field, and the radiation energy can be checked simultaneously in one single irradiation of the measuring block and subsequent reading of the measurement results.

3 Claims, 2 Drawing Sheets

MEASURING DEVICE FOR CHECKING RADIATION FIELDS FROM TREATMENT MACHINES FOR RADIOTHERAPY

In treatment of cancer tumours treatment machines for radiotherapy, e.g. linear accelerators, betatrons or cobalt units are often used to give a certain radiation dose to the tumour and its border zone. The radiation from such machines is usually photons or electrons in the energy range 0.5–45 MeV and the size of the radiation field is determined by adjustable collimators that can be matched to the extent of the intended treatment volume. The treatment machines are also equipped with an internal dose monitor (cobalt units usually have a timer instead) to control the radiation does that is given to a patient during a treatment.

The effect of radiation therapy is based on the fact that many types of tumour tissue under certain circumstances have a higher sensitivity to ionising radiation than normal tissue. The margin between the dose required to completely eliminate the tumour and the dose level that gives severe radiation damage in the normal tissue is however very small. For that reason it is crucial for the result of the treatment that the dose given to every part of the tumour volume is according to the therapist's prescription, and large resources are spent in measuring and calculating doses and dose distributions so that they agree with the treatment plan.

As planning and calculation of the radiation dose for the treatment is based on measured radiation field data for each treatment machine it is of course also important that the treatment machines in all respects maintain their radiation properties, and for that reason the most important radiation parameters are controlled regularly. If these parameters during a control are outside certain tolerances the treatment machine may not be used for treatment of patients before it has been repaired or adjusted so that it meets the set requirements again.

The most important radiation parameters are: the dose monitor calibration, the radiation energy, the radiation field homogeneity and the correspondence between the radiation field and the alignment tools that are used as for example field lights, cross-hairs or laser lines.

For measurements of these parameters the existing method is to use combinations of different types of measuring equipment such as ionisation chambers with electrometers, water phantoms or simple detector scanners with ionisation chambers or semiconductors as well as x-ray film with film evaluation equipment.

The dose monitor calibration is usually checked with an ionisation chamber or semiconductor detector placed at a specified depth in a plastic block. The block is placed at a fixed distance from the radiation source and irradiated with a certain number of monitor units and the dose monitor calibration is checked by comparing the measured dose with the reference value from the initial machine calibration.

The energy is usually checked by dose measurements similar to the dose monitor calibration procedure but with two measurements at different depths in the plastic block, e.g. 10 and 20 cm, and then calculating the ratio between these values and comparing with the reference value from the initial machine calibration. The energy can also be determined by scanning a detector in a water phantom, thereby obtaining a depth dose distribution, and calculating the dose ratio between two different depths from these values.

The homogeneity of the radiation field is usually checked by scanning a detector across the field at a specified depth in a water phantom and plotting the detector signal against position. The field profile curve that is obtained is then read at certain points between the field centre and the edge, and the relative percentage dose values in these points are used to characterise the dose homogeneity and these values are compared with the tolerance limits. This procedure is done for both main axes of the field, perpendicular to the beam axis.

The field profile curve may also be obtained with a scanner where the detector is mounted inside a build-up block and the entire block is scanned in air.

X-ray film may also be used so that the film is exposed in a plastic block, developed and then measured with a densitometer in the relevant points. The density values are related to the doses in these points and can thus be used for homogeneity determination.

The geometrical correspondence between the radiation field and the alignment tools at the machine is usually checked by placing an x-ray film in a light proof envelope in front of the machine. The edge of the light field and the laser lines or cross-hairs are then marked on the film with a sharp tool on the envelope surface, either as small holes in the envelope or as lines. The film is then exposed with the radiation field and developed. The exposed field is compared with the location of the marks on the film and the deviation is compared with the tolerance limits.

The measuring procedure with these techniques is however fairly time consuming and both measurement and interpretation of the results require good competence in radiation physics. This often makes the intervals between the quality controls significantly longer than desirable and technical problems in a treatment machine can affect the treatments of a large number of patients before they are discovered.

The present invention provides a measuring device for simultaneous checking of all the most important radiation parameters in one single procedure. The measurement procedure and the interpretation of the results becomes so simple and standardised with this device that performing it does not require any extensive training, and it is also so quick that checking of the treatment machines can be done daily or even more often if needed.

The measuring device of the invention comprises a measuring block from a suitable material, preferably a plastic material, with a number of radiation detectors, e.g. ionisation chambers or semiconductor detectors, that are mounted in specific locations in the block. In front of the detectors is material for dose buildup and formation of electron equilibrium and for one detector also filter material for energy checks. The radiation detectors are connected via a cable to a readout unit outside the treatment room where irradiation is done. In the readout unit the detector signals are processed and the measurement results are presented. The detector positions and the signal processing is selected in such a way that the radiation parameters of interest can be read directly from the readout unit.

For checking of a treatment machine the measuring block is placed at a fixed distance from the radiation source and is adjusted to proper position with the existing setup aids such as light field with cross-hairs or laser lines in the room. Then the block is irradiated with a predetermined setting of energy, field size and radiation dose. After the irradiation the radiation parameters are read directly at the readout unit. The obtained readings are compared with the tolerance limits for each parameter and form the basis for the judgement if the machine still can be used for patient treatment. The measured values are also usually recorded, either manually or by automatic recording of the measurement signals from the readout unit.

Figure 2:
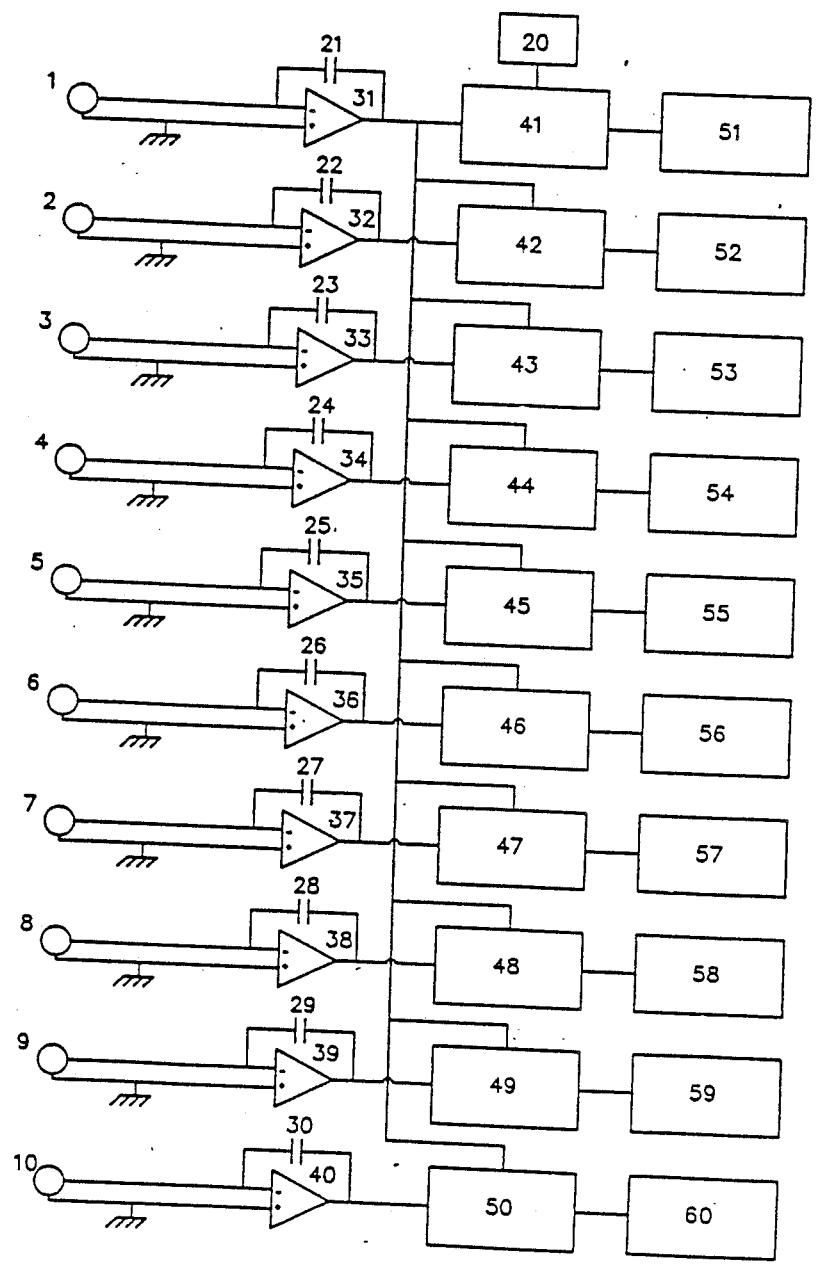

One example of an embodiment of the invention is described below and is illustrated in the accompanying drawings, where FIG. 1 shows the measuring block with detectors and FIG. 2 shows the circuit diagram of the readout unit.

In a measuring block 11 of polystyrene, with sufficient thickness to give even backscatter, ten radiation detectors 1–10 are placed in recesses in the top side of the block. Wires from the detectors are running in channels in the block to a connector 12, where the cable to the readout unit is connected. A cover plate of polystyrene 13, with sufficient thickness to provide electron equilibrium at the current radiation quality, covers the detectors and has field marking lines 14 for alignment with the light field and cross-hairs of the treatment machine. An energy filter 16 is placed in a recess 15 in the cover plate 13 for filtration of the radiation that reaches the detector 10. The detector 1 is connected to an electrometer amplifier 31 where the current from the detector is integrated in a capacitor 21. The voltage out from the electrometer amplifier is proportional to the accumulated charge in the capacitor 21 and then also proportional to the integrated dose in detector 1. This voltage is converted in an analog-to-digital converter 41 to a digital value that is displayed in a digital display 51. A constant reference voltage source 20 is used as reference voltage in the analog-to-digital converter, and the displayed value in the display 51 is then proportional to the absolute integrated dose in detector 1.

The remaining nine detectors 2–10 are connected to similar integrating electrometers 32–40, followed by analog-to-digital converters 42–50 and digital displays 52–60, but with the difference that the signal from the amplifier 31 is used as reference voltage for the analog-to-digital converters 42–50, which makes the values in the displays 52–60 proportional to the ratio between the dose in the corresponding detector and the dose in detector 1, which corresponds to the relative dose in these points.

When measuring with this device, the result in the display 51 will correspond directly to the absolute dose in detector 1 in the centre of the measuring block for a direct check of the dose monitor calibration.

The detectors 2–5 are inside the set radiation field but rather far away from the centre of the measuring block along the main axes of the radiation field. The displays 52–55 will then show the homogeneity of the radiation field along the different axes as percentage relative dose in the respective measuring points. The relative dose level should be close to 100% in these points and the tolerance values for homogeneity variations are usually in the order of 2–5%.

The detectors 6–9 are located exactly at the edge of the light field that is used for setup of the radiation field, indicated by the field marking lines 14 at the cover plate 13, and the relative dose in these detectors, that is read on the displays 56–59, is a very sensitive indication of the geometrical correspondence between the light field and the radiation field. The relative dose level should be about 50% but the dose gradient is typically around 5–10% per mm at the field edge, so deviations of one or two mm will give very clear indications. This means that the tolerance levels for dose deviations at the field edge should be ±10–20%.

The relative dose in the detector 10 that is read at the display 60 give a value of the radiation energy that in principle corresponds to the relative depth dose at a certain depth. This value depends both on the radiation energy and on the material and thickness of the energy filter 16. The energy filter should be made in such a way that the relative dose in detector 10 is about 50%, which gives optimal sensitivity to energy variations. A suitable choice for 8 MV photons is for example steel with a thickness of 25 mm.

Several alternative ways of construction according to the same basic idea are possible. The detectors may for example be placed in the block in different ways without changing the main principles, e.g. along the diagonals instead of the main axes, more or less detectors may be used and the materials in the block 11, the cover plate 13 and the filter 16 can also be varied.

The readout unit can also be constructed in several ways, e.g. with measurement of dose rate instead of integrated dose by using resistors instead of the capacitors 21–30. The ratio can be generated in an analog divider before the analog-to-digital conversion, or conversion to digital form can be made directly after the electrometer amplifiers and all the signal processing be done in a computer unit. The presentation of the measurement values can also be done in analog instruments or as signals for OK or not OK from comparator circuits with preset threshold values directly after the amplifiers.

I claim:

1. A measuring device for checking of radiation fields from treatment machines for radiotherapy, comprising a measuring block (11) containing radiation detector means (1–10) arranged under a cover plate (13) provided with field marking lines (14) and energy filter means (16), said detector means being connected to readout means for signal processing and presentation of measurement values, characterised in that said radiation detector means comprising:

total dose detector means (1) centrally located in the measuring block (11) for checking dose monitor calibration, homogeneity detector means (2–5) located between the central detector means (1) and the edges of the measuring block (11) for determination of the beam homogeneity by comparing the reading thereof with those of the total dose detector means (1), edge detector means (6–9) for determination of the geometrical correspondence between the radiation field and the light field for setup of the radiation field by comparison of the readings thereof with those of the total dose detector means (1), and energy detector means (10) arranged below said energy filter means (16) for determination of the beam energy by comparison of the readings thereof with those of the total dose detector means (1), the arrangement of the radiation detectors (1–10) in the block (11) and the signal processing in the readout means being such that the dose monitor calibration, the homogeneity of the radiation field, the geometrical correspondence of the radiation field and the light field, and the energy of the radiation of the treatment machine can be checked simultaneously in one single irradiation of the measuring block (11) and subsequent reading of the measurement results.

2. A measuring device according to claim 1, characterised in that said radiation detectors (1-10) are ionisation chambers.

3. A measuring device according to claim 1, characterised in that said radiation detectors (1-10) are semiconductor detectors.

* * * * *